United States Patent
Kibele et al.

(10) Patent No.: US 6,440,513 B1
(45) Date of Patent: Aug. 27, 2002

(54) FLAT TRANSDERMAL MEDICATED SELF-ADHESIVE PATCH

(75) Inventors: Ralf Kibele; Hans-Juergen Schlueter, both of Holzkirchen (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 09/319,399

(22) PCT Filed: Dec. 4, 1997

(86) PCT No.: PCT/EP97/06799
§ 371 (c)(1),
(2), (4) Date: Aug. 5, 1999

(87) PCT Pub. No.: WO98/25257
PCT Pub. Date: Jun. 11, 1998

(30) Foreign Application Priority Data

Dec. 4, 1996 (DE) .......................................... 196 50 329

(51) Int. Cl.$^7$ ............................. B32B 7/06; B32B 7/12; G09F 3/10; A61L 15/00; A61F 13/02; A61K 9/70

(52) U.S. Cl. .................... 428/40.1; 428/41.7; 428/42.2; 428/43; 428/343; 424/448; 424/449

(58) Field of Search ............... 428/40.1, 41.7, 428/42.2; 424/448, 449

(56) References Cited

U.S. PATENT DOCUMENTS

| | | | | |
|---|---|---|---|---|
| 2,235,436 A | * | 3/1941 | Laub ........................... | 600/556 |
| 4,564,010 A | * | 1/1986 | Coughlan et al. ........... | 128/156 |
| 4,943,435 A | * | 7/1990 | Baker et al. ................. | 424/448 |
| 5,599,289 A | * | 2/1997 | Castellana .................... | 602/57 |
| 5,950,830 A | * | 9/1999 | Trigger ....................... | 206/440 |
| 5,998,694 A | * | 12/1999 | Jensen et al. ................. | 602/57 |
| 6,051,249 A | * | 4/2000 | Samuelsen .................. | 424/443 |

* cited by examiner

Primary Examiner—Shrive P. Beck
Assistant Examiner—Elena Tsoy
(74) Attorney, Agent, or Firm—Frommer Lawrence & Haug LLP; Ronald R. Santucci

(57) ABSTRACT

The invention relates to a patch-shaped object, for example a TTS, patch, sticker or label, where the object comprises or is formed by an adhesive layer and a cover foil covering the adhesive layer having the same surface dimensions. The object further comprises a peeling foil temporarily covering the oppositely opposed side of the adhesive layer where the peeling foil extends beyond the patch-shaped object on all sides to form a border, the border having two recesses disposed at a spacing apart from one another. The end points of a break line formed in the peeling foil and passing over the object joins into each of the recesses.

23 Claims, 3 Drawing Sheets

FLAT TRANSDERMAL MEDICATED SELF-ADHESIVE PATCH

BACKGROUND OF THE INVENTION

Peeling aids for patches, transdermal therapeutic systems (TTS), stickers or labels are known for example from GB-A 2 179 910 and EP-B1 0 418 608. Such peeling aids are provided by partially straight or non-linear breaking lines or cuts in the carrier material (peeling foil) and are intended to simplify the mechanical removal of the objects from the carrier material.

Patches, for example transdermal therapeutic systems (TTS), are manufactured in several steps. Frequently, the drug or active agent and the additives are directly worked into the adhesive, so that an easily spreadable mass results containing the drug. This mass is then applied to the surface of a foil as the carrier or peeling foil of the patch, optionally dried and subsequently provided with a cover foil for the patch. It is necessary that such composites are then divided into smaller bands or strips for further processing. Finally, the patches are stamped out of the bands, where normally two gratings result along with the patches.

As an example, FIG. 1 illustrates a top view of a transparent composite comprising a cover foil and an adhesive layer (hatching from top right to left bottom) as well as a peeling foil (hatching from left top to right bottom). When one considers that the peeling foil is on the underside in the drawing plane, the break lines are stamped into the foil from below. According to FIG. 2, again in the drawing plane of the foil, circular cuts to define the patches are also stamped out and run in the axial direction of the band. The break lines cross over the so-defined patches, although the break lines are not interconnected with one another. Thereafter, according to FIG. 3b, the foil band is separated from the material of the cover foil with the adhesive layer, where the band for the carrier or the peeling foil with the individual patches remain as shown in FIG. 3a. Referring to FIG. 4a, cuts are then provided in the foil band of the carrier (peeling foil), which define the peeling foil of the individual patches, whereafter the individual patches are separated out of the foil band. There remains the foil band with the removed patches as shown in FIG. 4b as well as the patches themselves as shown in FIG. 5.

When stamping out such composites of cover foil, adhesive and peeling foil, the conventional stamping forms or dies frequently cause tears to arise in the grating, for example in the cross pieces shown in FIG. 4b. As the end points of the cuts or break lines approach one another, the cross pieces are particularly vulnerable at these locations, because the cross pieces are made as small as possible to save material.

The same problem exists when the break lines are continued into the cross pieces, as shown in the patch of DE-C 3 931 019 in FIG. 1 (not shown here), or the patch shown in FIG. 1 of DE-C 3 344 334 (not shown here) in which the break line 4 cuts into the cross piece. Finally, FIG. 1 of U.S. Pat. No. 4,413,621 illustrates a patch (not shown here) in which the break line 15 cuts into the cross piece.

SUMMARY OF THE INVENTION

The object of the present invention is then to provide a patch with peeling foil having a suitable cut or a suitable break line, whereby the described tearing of the cross pieces is avoided and the production yield of patches is increased.

According to the invention, a flat self-adhering drug patch is provided comprising a cover foil and self-adhesive layer containing at least one active agent, where the patch additionally comprises a removable carrier material (peeling foil) and where the carrier material extends beyond the patch with cover foil and self-adhesive layer to form a border, wherein the border is provided with two recesses spaced apart from one another, and wherein the respective end points of a break line extend from the recesses, the break line being formed in the carrier material and passing over the self-adhesive layer.

The patch may be a TTS by which the self-adhesive layer contains a drug or active agent.

According to the present invention, a flat self-adhering drug patch is also provided with a cover layer, reservoir containing at least one drug and a membrane which is self-adhesive or carries an adhesive, wherein the patch additionally comprises a removable carrier material (peeling foil) and wherein the carrier material extends beyond the patch with its cover foil as well as reservoir and membrane to form a border, wherein the border is provided with two recesses spaced apart from one another and wherein the end points of a break line extend from the recesses, the break line being formed in the carrier material and passing over the self-adhesive layer.

The recesses or cut-outs can be formed to be semi-circular or approximately V-shaped.

The patch can have multiple corners, in particular be square or rectangular or can be elliptical or circular and can be covered by the carrier (peeling foil) which has multiple corners, in particular is square or rectangular. The corners of the multi-cornered carrier can be rounded.

Furthermore, the patch according to the invention can be circular and be covered by a round, triangular, hexagonal or octagonal carrier (peeling foil).

The break lines can be formed as indentations or as a cut or they can also be formed by perforations.

In a preferred embodiment of the patch, the carrier (peeling foil) extends beyond the patch on all sides.

Finally, the patch according to the invention can be provided with bumps or knobs located in or on the carrier. Such bumps are adapted to simplify removal of the patch from a package.

A further embodiment of the invention relates to a method for manufacturing flat self-adhering drug patches according to the invention, including (a) providing a band of a multi-layer composite comprising a layer for the cover foil, a layer for the self-adhesive layer or the reservoir with membrane, and a layer for the removable carrier material (peeling foil), and providing break lines in the removable carrier material, (b) making cuts through the layer for the cover foil with the self-adhesive layer or with the reservoir and membrane to define the patches, the cuts made simultaneously or before or after, (c) making cuts in the layer for the removable carrier material (peeling foil), thereby defining the carrier material (peeling foil) of the patches, the cuts being made simultaneously or before or after, (d) (i) separating a band of the composite comprising the layer for the cover foil and the self-adhesive layer or the reservoir with membrane, whereby the patches are defined by the cuts in step (b)

(ii) separating a band of the removable the carrier material (peeling foil), whereby the carrier material (peeling foil) of each patch defined by the cuts according to step (c) is removed from the band, and (iii) separating flat self-adhering drug patches with removable carrier material (peeling foil).

The method according to the invention can be carried out in that one performs step (a), thereafter performs step (b), thereafter separates the band (d) (i), thereafter performs step (c) and thereafter separates the band (d) (ii) and the patches (d) (iii).

BRIEF DESCRIPTION OF THE DRAWINGS

The invention will be explained in more detail in the following in conjunction with the figures.

DETAILED DESCRIPTION OF THE PREFERRED EMBODIMENT

With the stamped forms shown in FIGS. 6 to 14, to be discussed below, the material consumption is greatly reduced and the stamping production could be greatly increased, through increased operational reliability (distinctly fewer tears in the band). For example, the intermediate space shown in FIGS. 6 to 8 was reduced to 40 to 60% of the original width (FIGS. 1 to 5).

Figure 4B:
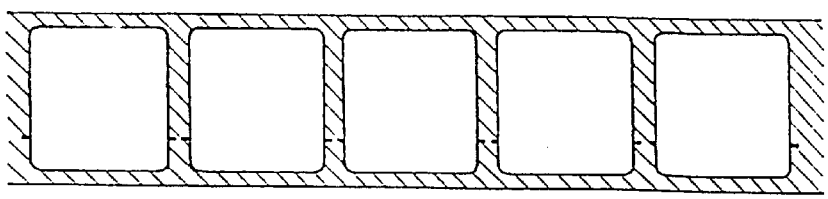
FIGS. 1 to 4b illustrate various stages in the production of conventional patches.
Figure 4A:
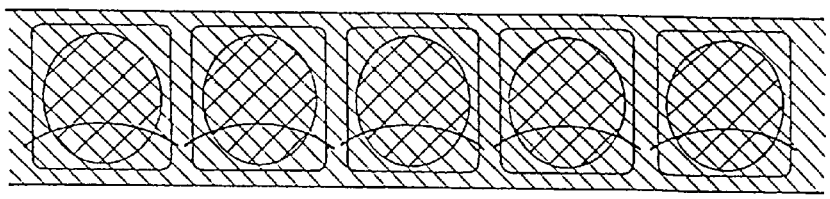
Figure 3B:
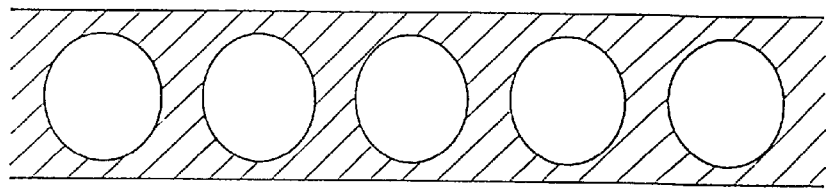
Figure 3A:
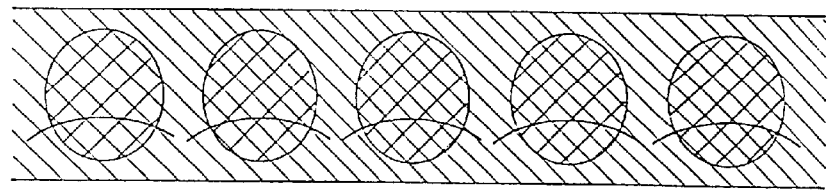
Figure 2:
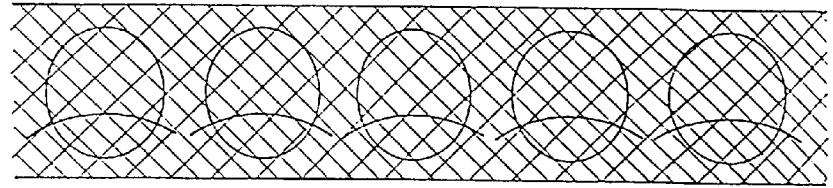
Figure 1:
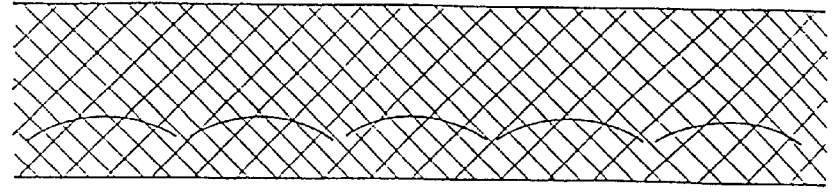
Figure 5:
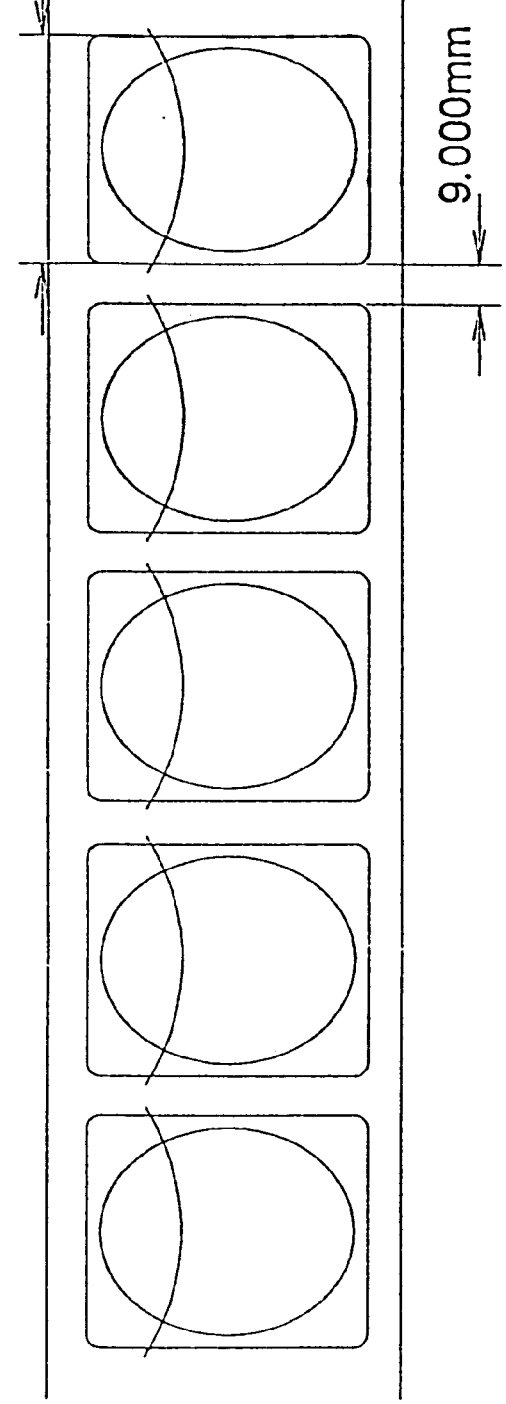
FIG. 5 shows a band analogous to that of FIG. 4a for another known patch.
Figure 6:
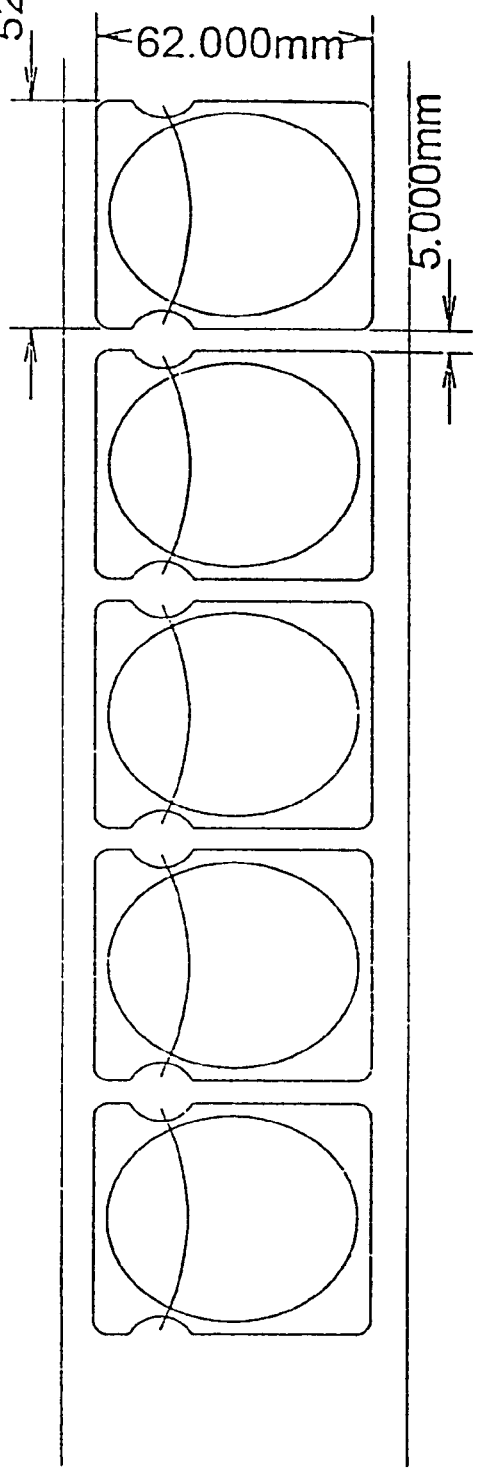
FIG. 6 shows a band analogous to FIGS. 4a and 5 for the production of patches according to the present invention.
Figure 7:
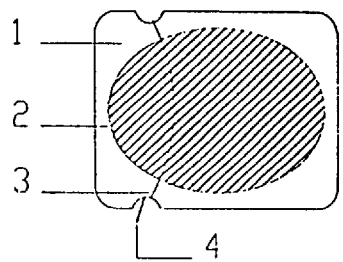
FIGS. 7 to 14 show patches according to the invention with their respective peeling foils.

With respect to the patch shown in FIG. 7, it was found that with the production of patches with the inventive recesses, the total amount of laminate could be reduced by 5 to 10%. This was possible because the cross pieces or intermediate portions necessary for separating the patches with their peeling foil could be reduced, which led to a considerable saving of material. This will be illustrated in the following with an example of a 20 cm², patch. In conventional stamping dies, an intermediate space of at least 9 mm is provided (FIG. 5) to guarantee reliable processing. In the stamping dies or forms of the present invention, this intermediate space could be reduced to 4 mm, namely with the same or better processing capabilities. With two patches each having an area of 20 cm², a reduction of the intermediate portions by 5 mm leads to a material saving of 8%.

The advantage of better utilisation or production yield in the stamping process results from the fact that any tear in the band leads to sticking or congestion on the stamp dies and therefore extensive cleaning efforts. If in the same production line, further steps such as printing or packaging the patches are carried out, subsequent problems are possible, if not expected (for example contamination of the sealing irons for hot-seal packaging foils by melting of the sealing layer). Normally, one can expect down times of 10 to 15 minutes for each band tear. For example, with commercial stroke stamping machines, an output rate of 100 to 120 per minute is common. Thus for every down time or interruption, a reduced production of 1500 to 3600 patches per band results.

The shape of the recesses according to the invention can be symmetrical or non-symmetrical and arc-shaped or triangular. When a rounded arc-shaped recess is provided, it is not necessary that the end of the break line or cut lie directly in the center of the arc. In the embodiment with a triangular recess, the end of the break line or cut, however, should extend rather exactly to the peak of the triangle.

The recesses according to the invention can be applied to any type of flexible peeling foil. For transdermal systems, a suitable peeling foil can be for example polyethylene terephthalate, polyethylene, polypropylene or polyvinylchloride or composite foils (for example paper/polyethylene), which are known in the art. The peeling foil can be provided with a separating agent coating, for example it can be treated with silicone or fluorosilicone.

The recesses according to the invention can be used in conjunction with arc-shaped, non-linear or partially linear and linear break lines or cuts. The recesses are not limited to a certain size of the peeling foil. Commercially available sizes of transdermal therapeutic systems lie for example between 5 and 100 cm², where the active surface can be round, oval or multi-cornered (optionally rounded).

Figure 8:
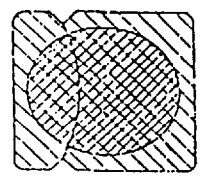
Figure 9:
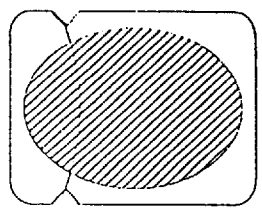
Figure 10:
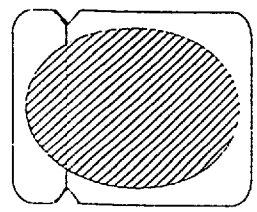
Figure 11:
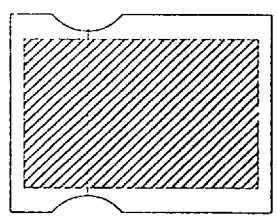
Figure 12:
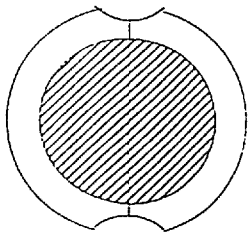
Figure 13:
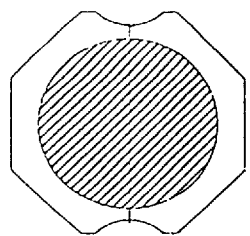
Figure 14:
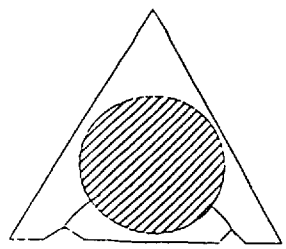

FIGS. 7 and 8 show patches according to the invention, which differ from the known patches of FIGS. 1 to 5 in that two oppositely disposed recesses are formed in the border of the peeling foil, where the break lines join into the recesses.

FIG. 7 shows a rectangular carrier or peeling foil 1, upon which the patch 2 is centrally arranged. Patch 2 is preferably a transdermal therapeutic system adhered to the peeling foil. The cut or break line 3 ends at the rounded recesses 4.

FIGS. 8 to 14 show further embodiments of the patch according to the invention.

What is claimed is:

1. A flat self-adhering drug patch comprising a cover foil and self-adhesive layer containing at least one active agent, where the patch additionally comprises a removable carrier material and where the carrier material extends beyond the patch with cover foil and self-adhesive layer to form a border, wherein the border is provided with two recesses spaced apart from one another, and wherein the respective end points of a break line extend from the recesses, the break line being formed in the carrier material and passing over the self-adhesive layer.

2. A patch according to claim 1, comprising a transdermal therapeutic system including the drug-containing self-adhesive layer.

3. A patch according to claim 1, wherein the recesses are approximately semi-circular or V-shaped.

4. A patch according to claim 1, wherein the patch shape is selected from the group consisting of a polygon, rectangular, ellipse and circle, and covered with a carrier material having a shape selected from the group consisting of a polygon, a square and a rectangular.

5. A patch according to claim 1, the patch being approximately circular and covered with a round, triangular, hexagonal or octagonal carrier material.

6. A patch according to claim 1, wherein the break line is formed as an indentation, a cut, or a perforation.

7. A patch according to claim 1, wherein the carrier material extends beyond all sides of the patch.

8. A patch according to claim 1, wherein bumps are provided in or on the carrier material.

9. A method for manufacturing a flat self-adhering drug patch according to claim 1 including:

(a) providing a band of a multi-layer composite, comprising:

a layer for the cover foil;

a layer for the self-adhesive layer;
a layer for the removable carrier material; and
break lines in the removable carrier material;

(b) making cuts through the layer for the cover foil with the self-adhesive layer to define the patches;

(c) making cuts in the layer for the removable carrier material, thereby defining the carrier material of the patches;

(d) (i) separating a band of the composite comprising the layer for the cover foil and the self-adhesive layer, whereby the patches are defined by the cuts in step (b);
   (ii) separating a band of the removable carrier material, whereby the carrier material of each patch defined by the cuts according to step (c) is removed from the band; and
   (iii) separating flat self-adhering drug patches with removable carrier material, wherein the border of the carrier material which extends beyond the patch with cover foil and self-adhesive layer is provided with two recesses spaced apart from one another, and a break line formed in the carrier material and passing over the self-adhesive layer, wherein the respective end points of a break line extend from the recesses.

10. A method according to claim 9, wherein the cuts made through the layer for the cover foil with the self-adhesive layer to define the patches are selected from the group of cuts carried out simultaneously, in advance of or after providing a band of a multi-layer composite, comprising:
   a layer for the cover foil;
   a layer for the self-adhesive layer;
   a layer for the removable carrier material; and
   break lines in the removable carrier material.

11. A method according to claim 9, wherein the cuts made in the layer for the removable carrier material, thereby defining the carrier material of the patches are selected from the group of cuts carried out simultaneously, in advance of or after providing a band of a multi-layer composite, comprising:
   a layer for the cover foil;
   a layer for the self-adhesive layer;
   a layer for the removable carrier material; and
   break lines in the removable carrier material; and simultaneously, in advance of or after making cuts through the layer for the cover foil with the self-adhesive layer to define the patches.

12. A method according to claim 9, comprising:
providing a band of a multi-layer composite, comprising:
   a layer for the cover foil;
   a layer for the self-adhesive layer;
   a layer for the removable carrier material; and
   break lines in the removable carrier material;
making cuts through the layer for the cover foil with the self-adhesive layer to define the patches;
separating a band of the composite comprising the layer for the cover foil and the self-adhesive layer, whereby the patches are defined by making cuts through the layer for the cover foil with the self-adhesive layer to define the patches;
making cuts in the layer for the removable carrier material, thereby defining the carrier material of the patches;
separating a band of the removable carrier material, whereby the carrier material of each patch defined by making cuts in the layer for the removable carrier material, thereby defining the carrier material of the patches is removed from the band; and
separating flat self-adhering drug patches with removable carrier material.

13. A flat self-adhering drug patch with a cover layer, reservoir containing at least one drug and a membrane which is self-adhesive or carries an adhesive,
   wherein the patch additionally comprises a removable carrier material, and
   wherein the carrier material extends beyond the patch with its cover foil as well as reservoir and membrane to form a border; wherein the border is provided with two recesses spaced from one another and wherein the end points of a break line extend from the recesses, the break line being formed in the carrier material and passing over the self-adhesive layer.

14. A patch according to claim 13, wherein the recesses are approximately semi-circular or V-shaped.

15. A patch according to claim 13, wherein the patch shape is selected from the group consisting of a polygon, rectangular, ellipse and circle, and covered with a carrier material having a shape selected from the group consisting of a polygon, a square and a rectangular.

16. A patch according to claim 13, the patch being approximately circular and covered with a round, triangular, hexagonal or octagonal carrier material.

17. A patch according to claim 13, wherein the break line is formed as an indentation, a cut, or a perforation.

18. A patch according to claim 13, wherein the carrier material extends beyond all sides of the patch.

19. A patch according to claim 13, wherein bumps are provided in or on the carrier material.

20. A method for manufacturing a flat self-adhering drug patch according to claim 13, including:
   (a) providing a band of multi-layer composite comprising:
      a layer for the cover foil;
      a layer for the reservoir with membrane;
      a layer for the removable carrier material; and
      break lines in the removable carrier material;
   (b) making cuts through the layer for the cover foil with the reservoir and membrane to define the patches;
   (c) making cuts in the layer for the removable carrier material, thereby defining the carrier material of the patches; and
   (d) (i) separating a band of the composite comprising the layer for the cover foil and the self-adhesive layer, whereby the patches are defined by the cuts in step (b);
      (ii) separating a band of the removable carrier material, whereby the carrier material of each patch defined by the cuts according to step (c) is removed from the band; and
      (iii) separating the flat self-adhering drug patches with removable carrier material, wherein the border of the carrier material which extends beyond the patch with cover foil and self-adhesive layer is provided with two recesses spaced apart from one another, and a break line formed in the carrier material and passing over the self-adhesive layer, wherein the respective end points of a break line extend from the recesses.

21. A method according to claim 20, wherein the cuts made through the layer for the cover foil with the reservoir and membrane to define the patches are selected from the group of cuts carried out simultaneously, in advance of or after providing a band of multi-layer composite comprising:
   a layer for the cover foil;
   a layer for the reservoir with membrane;

a layer for the removable carrier material; and break lines in the removable carrier material.

22. A method according to claim 20, wherein the cuts made in the layer for the removable carrier material, thereby defining the carrier material of the patches are selected from the group of cuts carried out simultaneously, in advance of or after providing a band of multi-layer composite comprising:

a layer for the cover foil;

a layer for the reservoir with membrane;

a layer for the removable carrier material; and break lines in the removable carrier material;

and simultaneously, in advance of or after making cuts through the layer for the cover foil with the reservoir and membrane to define the patches.

23. A method according to claim 20, comprising:

providing a band of multi-layer composite comprising:
- a layer for the cover foil;
- a layer for the reservoir with membrane;
- a layer for the removable carrier material; and
- break lines in the removable carrier material;

making cuts through the layer for the cover foil with the reservoir and membrane to define the patches;

separating a band of the composite comprising the layer for the cover foil and the self-adhesive layer, whereby the patches are defined by the cuts made through the layer for the cover foil with the reservoir and membrane to define the patches;

making cuts in the layer for the removable carrier material, thereby defining the carrier material of the patches;

separating a band of the removable carrier material, whereby the carrier material of each patch defined by the cuts made in the layer for the removable carrier material, thereby defining the carrier material of the patches is removed from the band; and separating the flat self-adhering drug patches with removable carrier material.

\* \* \* \* \*